(12) United States Patent
Sixto, Jr. et al.

(10) Patent No.: US 8,419,745 B2
(45) Date of Patent: Apr. 16, 2013

(54) BONE PLATE BENDER SYSTEM

(75) Inventors: Robert Sixto, Jr., Miami, FL (US); Jose Luis Francese, Miami Springs, FL (US); Juergen A. Kortenbach, Miami Springs, FL (US)

(73) Assignee: Biomet C.V., Gibraltar (GI)

( * ) Notice: Subject to any disclaimer, the term of this patent is extended or adjusted under 35 U.S.C. 154(b) by 369 days.

(21) Appl. No.: 12/766,539

(22) Filed: Apr. 23, 2010

(65) Prior Publication Data

US 2011/0264100 A1    Oct. 27, 2011

(51) Int. Cl.
*A61B 17/88* (2006.01)

(52) U.S. Cl.
USPC ............................................................ 606/101

(58) Field of Classification Search ............... 606/86 A, 606/86 B, 96–99, 101–104
See application file for complete search history.

(56) References Cited

U.S. PATENT DOCUMENTS

| | | | |
|---|---|---|---|
| 4,304,117 A * | 12/1981 | Rawson | 72/388 |
| 4,905,680 A | 3/1990 | Tunc | |
| 5,113,685 A * | 5/1992 | Asher et al. | 72/458 |
| 5,601,553 A | 2/1997 | Trebing et al. | |
| D383,841 S * | 9/1997 | Runciman | D24/133 |
| 5,690,631 A | 11/1997 | Duncan et al. | |
| 5,709,686 A | 1/1998 | Talos et al. | |
| 5,957,927 A * | 9/1999 | Magee et al. | 606/99 |
| 5,984,925 A | 11/1999 | Apgar | |
| 6,077,271 A * | 6/2000 | Huebner et al. | 606/101 |
| 6,193,721 B1 | 2/2001 | Michelson | |
| 6,283,969 B1 | 9/2001 | Grusin et al. | |
| 6,602,255 B1 | 8/2003 | Campbell et al. | |
| 6,866,665 B2 | 3/2005 | Orbay | |
| 6,960,211 B1 | 11/2005 | Pfefferle et al. | |
| 7,128,744 B2 | 10/2006 | Weaver et al. | |
| 7,179,260 B2 | 2/2007 | Gerlach et al. | |
| 7,229,446 B2 * | 6/2007 | Capanni | 606/86 R |
| 7,273,481 B2 | 9/2007 | Lombardo et al. | |
| 7,488,331 B2 * | 2/2009 | Abdelgany | 606/109 |
| 7,776,047 B2 * | 8/2010 | Fanger et al. | 606/96 |
| 7,935,126 B2 * | 5/2011 | Orbay et al. | 606/101 |
| 8,043,298 B2 * | 10/2011 | Capanni | 606/101 |
| 2002/0156474 A1 | 10/2002 | Wack et al. | |
| 2004/0210220 A1 | 10/2004 | Tornier | |

(Continued)

FOREIGN PATENT DOCUMENTS

DE    4343117 A1    6/1995
EP    1211992 B1    1/2004

(Continued)

*Primary Examiner* — Kevin T Truong
*Assistant Examiner* — Christopher Beccia
(74) *Attorney, Agent, or Firm* — Gordon & Jacobson, PC

(57) ABSTRACT

A pair of plate benders are provided for bending a bone plate. Each bender includes a lever arm having a first end and a second end. The first end includes a fulcrum for placement on the upper surface of the plate, and a foot insertable through the oblong screw hole to contact the lower surface of the plate. The second end includes a cut-out with a central divider. The cut-out has a length dimensioned to extend widthwise about the plate at the location of the oblong screw hole with the divider extending into the oblong screw hole for stability. The second end may also be provided with a deep slot that accommodates the thickness of the plate. In use, plate benders with such structure can be used in pairs to longitudinal bend the plate; bend the plate in plane; or twist the plate along its axis.

29 Claims, 13 Drawing Sheets

U.S. PATENT DOCUMENTS

| | | |
|---|---|---|
| 2005/0192577 A1 | 9/2005 | Mosca et al. |
| 2005/0251138 A1 | 11/2005 | Boris et al. |
| 2006/0052789 A1 | 3/2006 | Knopfle et al. |
| 2006/0161158 A1 | 7/2006 | Orbay et al. |
| 2007/0203492 A1* | 8/2007 | Needham et al. ............... 606/61 |
| 2007/0233112 A1 | 10/2007 | Orbay et al. |
| 2007/0269544 A1 | 11/2007 | Erickson et al. |
| 2008/0275447 A1 | 11/2008 | Sato et al. |
| 2009/0012571 A1 | 1/2009 | Perrow et al. |
| 2009/0118768 A1 | 5/2009 | Sixto, Jr. et al. |
| 2009/0118769 A1 | 5/2009 | Sixto, Jr. et al. |
| 2009/0118770 A1 | 5/2009 | Sixto, Jr. et al. |
| 2009/0125069 A1 | 5/2009 | Sixto, Jr. et al. |
| 2009/0125070 A1 | 5/2009 | Sixto, Jr. et al. |
| 2009/0312759 A1 | 12/2009 | Ducharme et al. |
| 2009/0318979 A1* | 12/2009 | Raines et al. ................. 606/291 |
| 2011/0092981 A1* | 4/2011 | Ng et al. ...................... 606/101 |

FOREIGN PATENT DOCUMENTS

| | | |
|---|---|---|
| EP | 1423057 B1 | 12/2006 |
| EP | 1882452 A1 | 1/2008 |
| EP | 1882453 A1 | 1/2008 |
| EP | 1654994 B1 | 4/2008 |
| WO | WO2005044121 A1 | 5/2005 |
| WO | WO2005/079428 | 9/2005 |
| WO | WO2006047581 A2 | 5/2006 |
| WO | WO2009058960 A2 | 5/2009 |

* cited by examiner

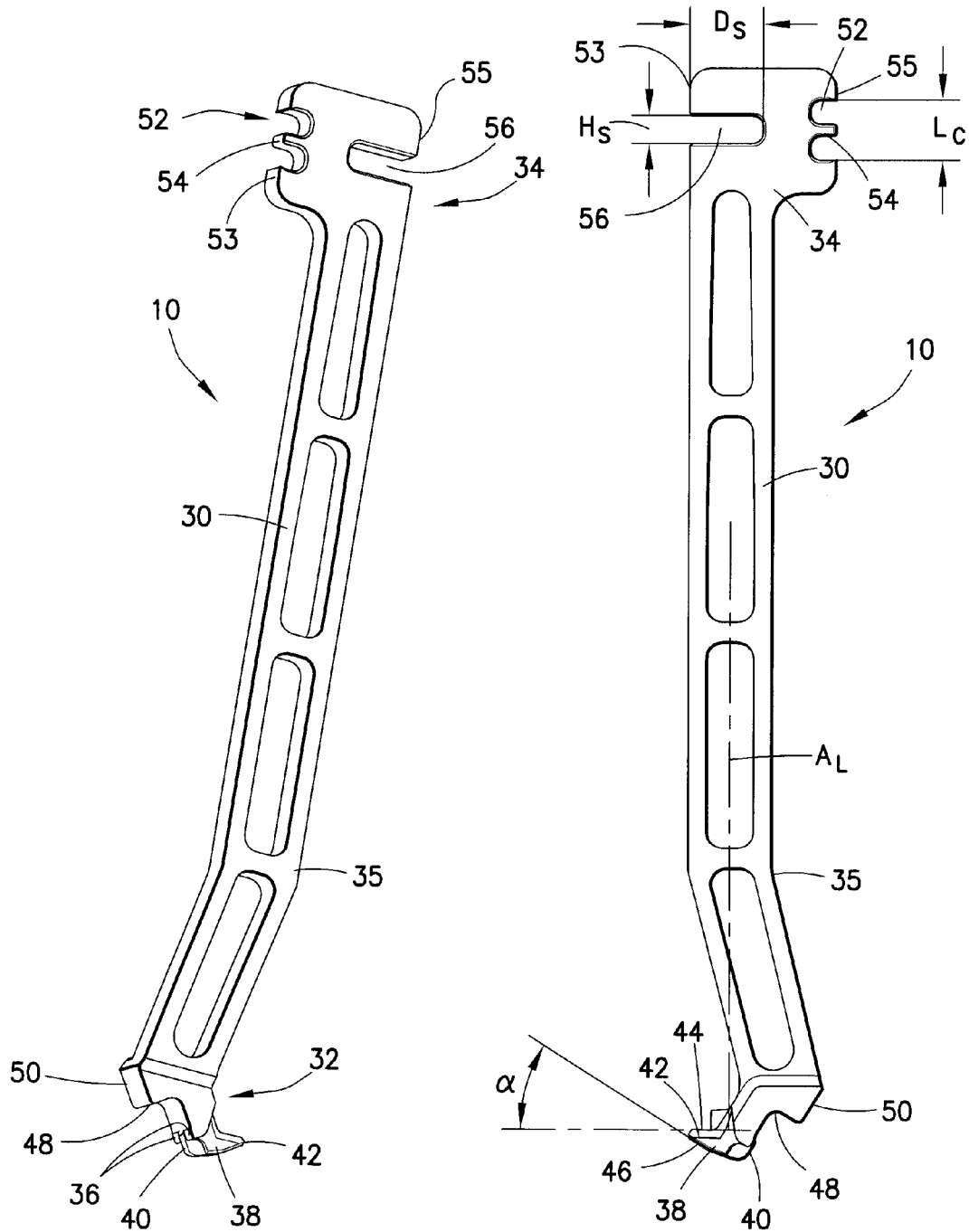

BONE PLATE BENDER SYSTEM

BACKGROUND OF THE INVENTION

1. Field of the Invention

This invention relates broadly to a system of a bone plate and instruments for use therewith, as well as methods for implanting bone plates. More particularly, this invention relates to systems and methods for bending bone plates.

2. State of the Art

The long bones of the upper extremity are the humerus, radius and ulna. The distal portion of the humerus and the proximal portions of the radius and the ulna form the elbow joint. The functional outcomes of elbow fractures often include high rates of joint stiffness, loss of range of motion and non-union.

Orthopedic surgeons generally follow certain principles for the internal fixation of fractures of the upper extremity, particularly those fractures surrounding the elbow joint. Each screw used to attach the plate to the bone should be as long as possible and engage as many articular fragments as possible. The screws should lock to the plate and interdigitate to create a "fixed angle" structure. The plate must be strong and sufficiently stiff to not break or bend under load. And the plate should correspond to the anatomical contours of the surface of the bone to distribute the load. Adhering to these principles for elbow fracture repair is particularly challenging given the difficulty of the surgical procedure and the anatomical variation among patients.

A bone plate attached to the surface of a fractured bone of the elbow joint may tend to stand "proud" of the bone surface, as many currently available plates do not fit well on the bone surface without impinging on soft tissue or obstructing the natural articulation of the joint. One bone plate shape, even if provided for each type of elbow fracture and in different sizes, cannot accommodate all the anatomical differences among patients.

SUMMARY OF THE INVENTION

In accord with the invention, a system including a bone plate and plate bender is provided. The bone plate may be a fragment plate for treatment of a fracture along a bone of an upper extremity, and particularly of the elbow. The plate has an upper surface, a lower surface, a thickness defined by the distance between the upper and lower surfaces, and a longitudinal axis, and a width transverse to the longitudinal axis. A plurality of preferably non-threaded oblong screw holes pass through the upper and lower surfaces, with the oblong hole at the upper surface defining a major diameter and a relatively transverse minor diameter. In one embodiment, the oblong screw holes define relief at the lower plate surface in alignment with the major diameter of the screw hole. A plurality of threaded circular screw holes are preferably in a substantially alternating arrangement with the oblong screw holes along portions of the plate. Drill guides are preassembled into the threaded screw holes to facilitate drilling holes coaxially through the respective axes of the threaded screw holes when the lower surface of the bone plate is placed toward the bone. After such drilling, the guides are removable from the plate to permit insertion of a fixed-angle threaded fastener into the plate and bone.

Plate benders are provided for bending the plate. Each bender includes an elongate lever arm having a first end and an opposite second end. The first end includes a fulcrum for placement on the upper surface of the plate, and a foot insertable through the oblong screw hole to contact the lower surface of the plate. The first end includes an elevated portion elevated relative to the upper surface of the plate when the foot is inserted through the oblong screw hole. In addition, a stop is provided at the first end of the lever arm to limit or prevent certain bender movement.

The second end of the lever arm includes a cut-out with a central divider. The cut-out has a length dimensioned to extend widthwise about the plate at the location of an oblong screw hole in a relatively close engaging manner with the plate, with the divider extending into the oblong screw hole. In addition, a deep slot may be provided opposite the divided cut-out. The deep slot has a height and depth dimensioned such that the slot can be extended over the thickness of the plate and preferably receive substantially the entire width of the plate.

In use, the plate benders are used in pairs to permit longitudinally bending of the plate (either concavely or convexly relative to the upper surface of the plate) by attaching the first ends of a pair of benders to the plate and applying relative force to the lever arms such that the lower surface of the plate is forced upward relative to the fulcrum; in plane bending, by attaching the cut-outs of the second ends of a pair of a benders along the upper surface of the plate and applying an in-plane force to the lever arms; or twisting of the plate, by coupling the second ends of the pair of benders to the plate at the slots and applying a relative torque between the lever arms. The longitudinal and in-plane bending can be applied to the plate with the lower surface of the plate positioned against or substantially against the bone.

A particular advantage of the benders is that they may be used to apply longitudinal bending even while the plate is assembled with drill guides along a portion or all of its length. The elevated portion at the first end is dimensioned to be positioned over a drill guide assembled within a threaded hole adjacent the oblong hole in which the foot is inserted without interfering with the drill guide. In addition, the stop at the first end prevents a pair of plate benders positioned in immediately proximate oblong screw holes (with only a single intervening threaded screw hole) from applying a force that would effect convex longitudinal bending of the plate (relative to the upper surface) across the intervening threaded hole which could result in deformation of the threads of such hole and consequently preventing insertion of a threaded fastener. If a pair of benders are inserted at oblong holes surrounding a threaded hole and oriented to apply a force which could cause such deformation, the stops abut each other and prevent movement of the plate benders and the plate-deforming longitudinal force.

Additional objects and advantages of the invention will become apparent to those skilled in the art upon reference to the detailed description taken in conjunction with the provided figures.

BRIEF DESCRIPTION OF THE DRAWINGS

FIG. 1 is a perspective view of a plate bender according to a first embodiment of the invention.

FIG. 2 is a side elevation view of a plate bender according to a first embodiment of the invention.

DETAILED DESCRIPTION OF THE PREFERRED EMBODIMENTS

Turning now to FIGS. 1 through 5, a plate bender system comprising a plate bender 10 and an associated elongate bone plate 12 (FIG. 5) is shown. The plate bender is provided to adapt and particularly bend the plate to correspond to the anatomy of the bone of a patient on which the plate will be used. The plate 12 is an olecranon plate for treatment of a fracture along the olecranon bone. The olecranon plate is presented by way of example only, and other elongate bone plates for stabilization of fractures along other bones of the upper extremities along be used with a bender of the system as well.

Figure 5:
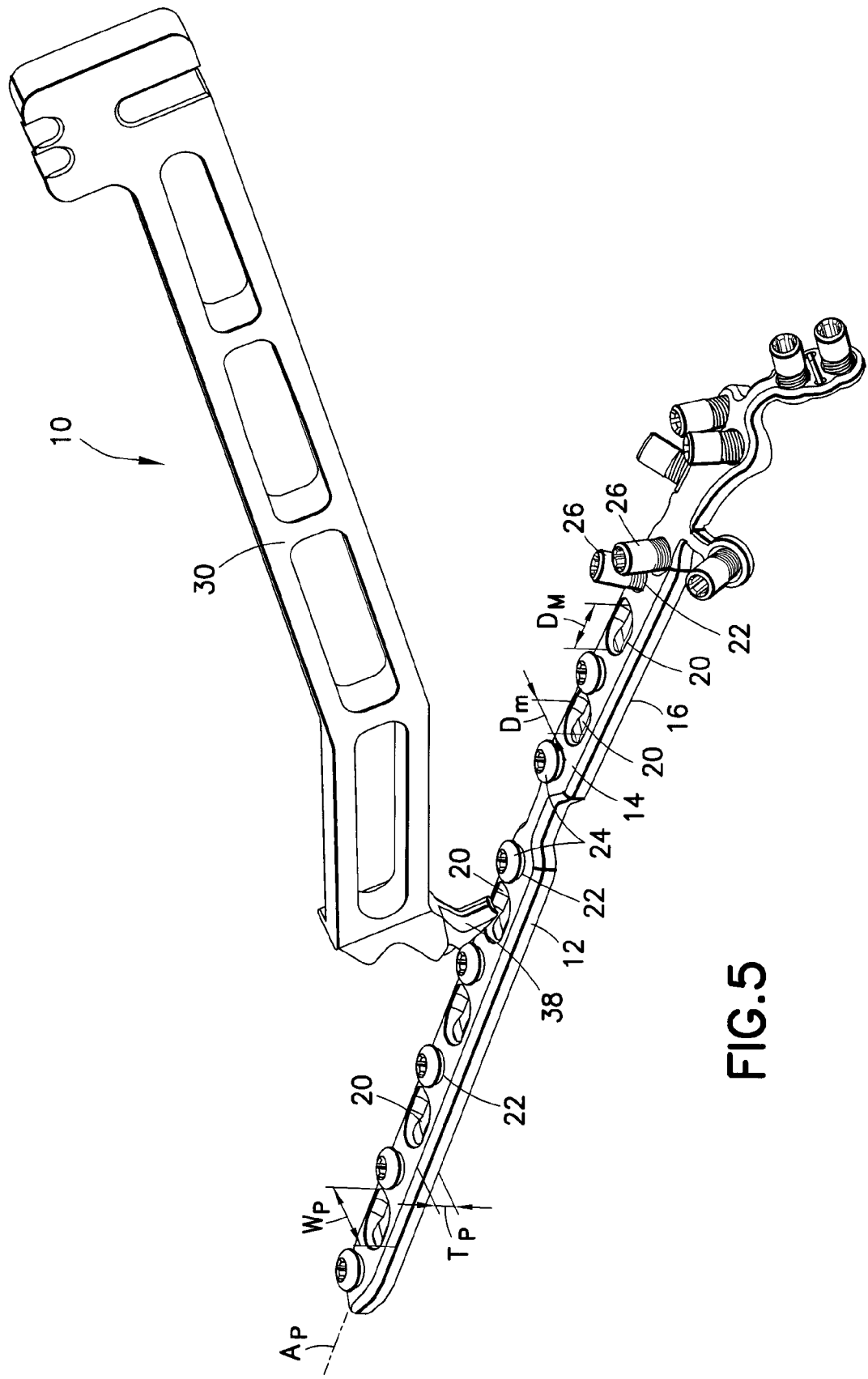
FIG. 5 is a perspective view of the first embodiment of the plate bender as it is assembled to a bone plate.
Figure 6:
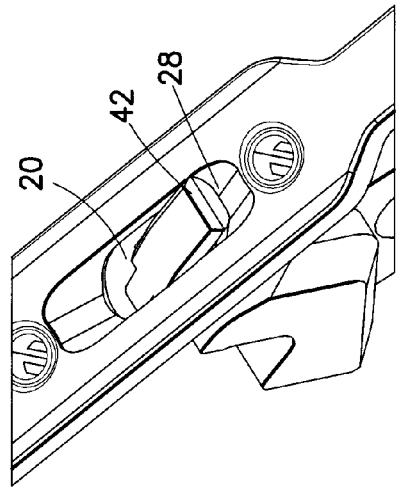
FIGS. 6 through 9 illustrate engagement of the foot at the first end of the plate bender at an oblong hole of the plate.

Referring specifically to FIG. 5, the plate 12 has an upper surface 14, a lower surface 16, a thickness $T_P$ defined by the distance between the upper and lower surfaces, a longitudinal axis $A_P$, and a width $W_P$ transverse to the longitudinal axis. A plurality of preferably non-threaded oblong screw holes 20 pass through the upper and lower surfaces, with the upper surface defining a major diameter $D_M$ and a relatively transverse minor diameter $D_m$ for each oblong screw hole 20. The ends of the oblong screw holes 20 are provided with relief portions 28 (FIG. 6) at the lower surface 16 of the plate 12 in alignment with the major diameter $D_M$ of the holes. The wall 29 of the relief portions 28 extending from the lower surface toward the upper surface is preferably angled at 30°±10° (FIG. 6). A plurality of threaded circular screw holes 22 are preferably in a substantially alternating arrangement with the oblong screw holes 20 along portions of the plate 12. Short drill guides 24 and tall drill guides 26 are preassembled into the threaded screw holes 22 to facilitate drilling holes coaxially through the respective axes of the threaded holes when the bone plate is placed against the bone. After such drilling, the guides are removable from the plate to permit insertion of a fixed-angle fastener (not shown) into the plate and bone. It is anticipated that such fixed-angle fasteners will have a head portion provided with machine threads for threadably engaging the threaded holes in the plate, and a threaded shaft provided with cortical threads for engaging the bone.

Referring back to FIGS. 1-5, the plate bender 10 is machined from a unitary piece of metal, such as titanium or stainless steel alloy bar stock. The bender 10 includes an elongate lever arm 30 extending primarily along an axis $A_L$ (FIG. 2). The lever arm 30 has a first end 32 and an opposite second end 34. The lever arm 30 is angled at 35, preferably adjacent the first end 32, to ergonomically orient the second end 34 of the bender for increased mechanical advantage during use. The first end 32 includes two shoulders 36 defining a fulcrum, and a foot 38 having a heel 40 extending below the shoulders 36. The foot 38 tapers to a toe 42. The toe 42 has an upper surface 44 that is preferably perpendicular relative to the lever arm axis $A_L$, and a lower surface 46 that is at an angle α relative to the upper surface 44, where α=30°±10°; together the upper and lower surfaces 44, 46 define a wedge.

Figure 7:
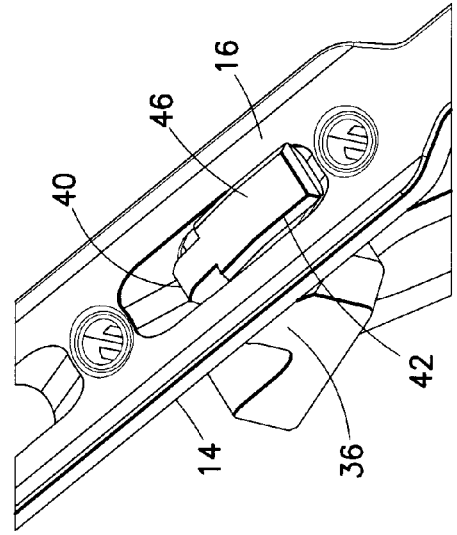
Figure 8:
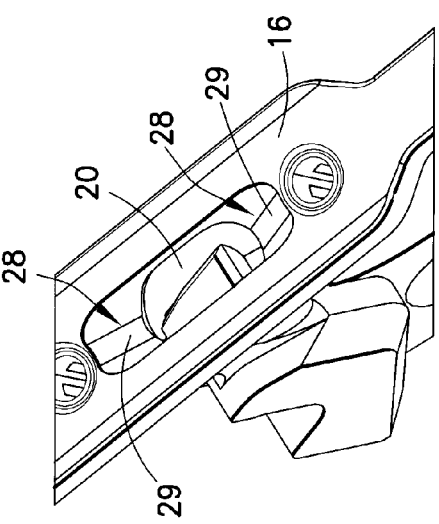
Figure 9:
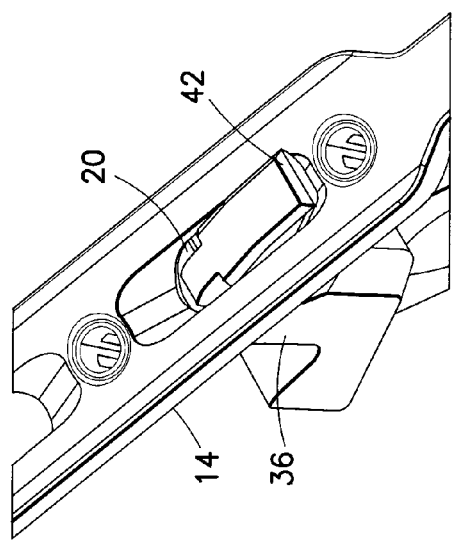

Referring to FIGS. 6-9, the foot 38 is sized to be received through an oblong bone screw hole 20 in the plate 12, with the toe 42 inserted longitudinally through the oblong screw hole (FIG. 6) and under one of the relief portions 28 at the end of the hole 20 (FIG. 7). The lever arm 30 is rotated to guide the toe 42 fully under the relief portion 28 and to seat the shoulders 36 on the upper surface 14 of the plate (FIGS. 8-9). The relative angles of the upper surface 44 and the lower surface 46 of the toe 42 allow the upper surface 44 to engage the wall 29 of the relief portion 28 of the plate, and the lower surface 46 of the toe 42 to extend substantially co-planar with the lower surface 16 of the plate 12 or to just very slightly protrude thereunder (FIG. 9). As such, foot 38 can be attached to the plate 12 even when the lower surface 16 of the plate is seated proximate or in contact with a bone. When the foot 38 is completely inserted into the oblong screw hole 20, the heel 40 seats at the rear of the screw hole 20 (opposite the toe 42) to provide a close fit and eliminate play, and the shoulders 36 seat on the upper surface 14 of the plate.

Figure 3:
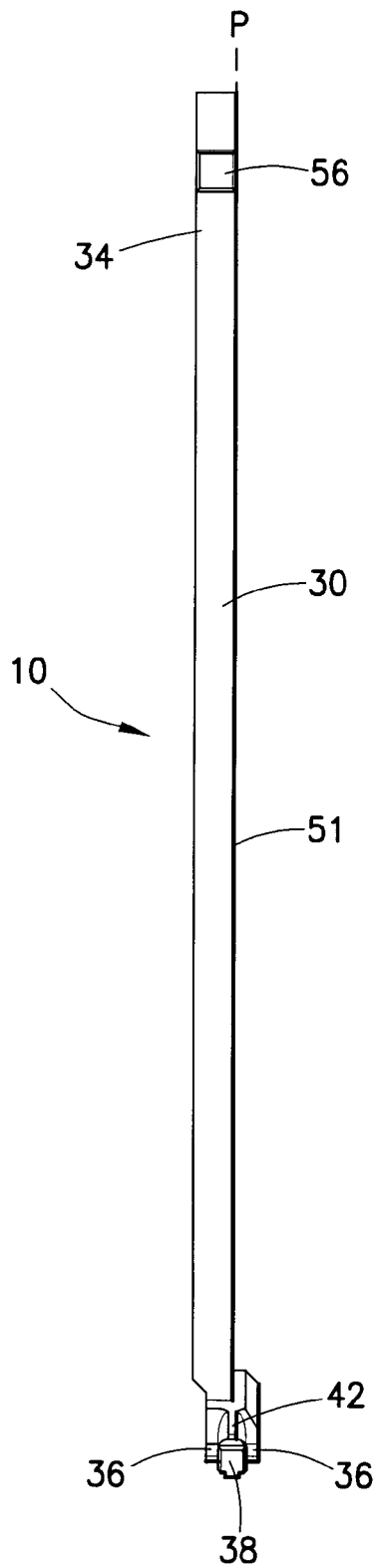
FIG. 3 is a first lateral view of a plate bender according to a first embodiment of the invention.
Figure 4:
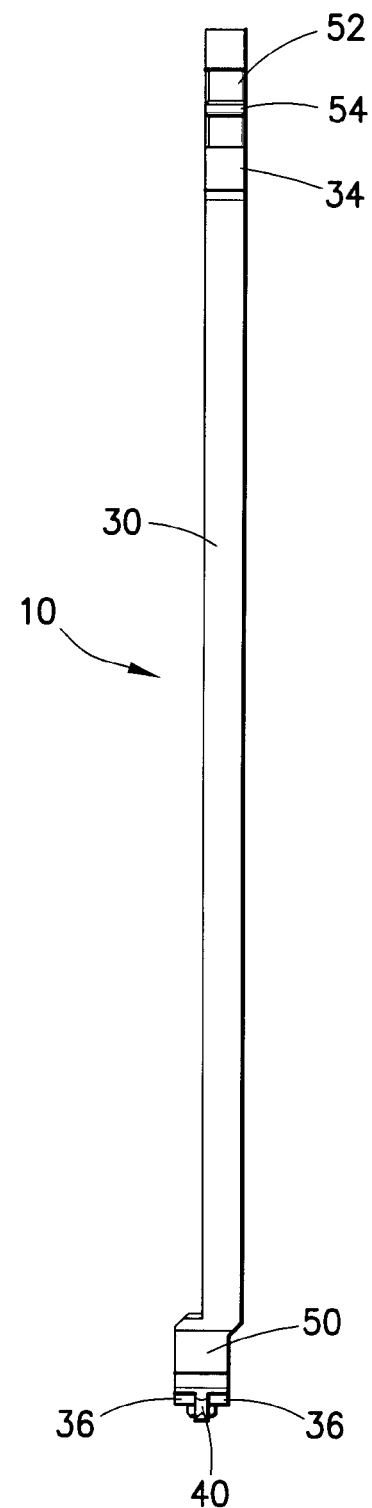
FIG. 4 is a second lateral view of a plate bender, opposite the first lateral view, according to a first embodiment of the invention.

Turning back to FIGS. 1-4, the first end 32 is structured with an undercut 48 over the shoulders 36. A stop 50 is also provided at the first end 32 of the lever arm 30 opposite the toe 42 and over the undercut 48. The lever arm 30 is laterally offset relative to the fulcrum (shoulders 36) and toe 42 such that a plane P extending parallel to the axis $A_L$ and through one side 51 of the lever arm 30 extends between the shoulders 36 and preferably bisects the foot 38 (FIG. 3).

The second end 34 of the lever arm 30 includes a first side 53 and an opposing second side 55. The first side 53 has a cut-out 52 with a central divider 54. As seen in FIG. 2, the cut-out 52 is has a length $L_C$. As described in more detail below, length $L_C$ is dimensioned to extend widthwise about the width $W_P$ of the plate 12 at the location of an oblong screw hole 20 in a relatively close engaging manner with the plate, with the divider 54 extending into the oblong screw hole. In addition, the second side 55 may be provided with a deep slot 56 preferably oriented opposite the divided cut-out 52. The deep slot 56 has a height $H_S$ and depth $D_S$ dimensioned such that the slot can be extended over the thickness $T_P$ of the plate 12. Preferably, the depth $D_S$ allows substantially the entire width $W_P$ (at least 80%) of the plate to be received in the slot. More preferably, the depth $D_S$ allows the entire width $W_P$ (100%) of the plate to be received in the slot, with the greater amount of the plate received in the slot permitting greater stability when torsionally bending the plate, as described further below.

In use, the plate benders can be used in pairs to longitudinally bend the plate (either concavely or convexly relative to the upper surface 14 of the plate) by attaching the first ends 32 of the pair of benders to two longitudinally displaced oblong screw holes 20 of the plate, in the manner shown in FIGS. 5-9, and applying relative force to the lever arms 30.

Figure 10:
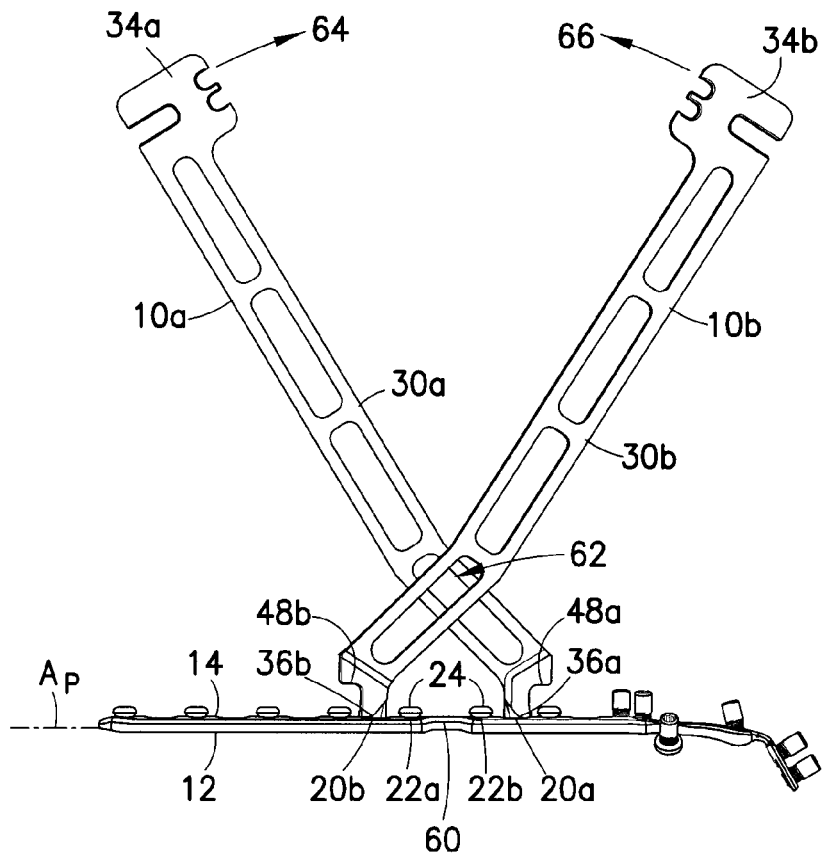
FIG. 10 illustrates an assembly of a pair of plate benders according to a first embodiment of the invention coupled to the plate in a first arrangement.

More particularly, referring to FIG. 10, a pair of benders 10a, 10b is shown attached to oblong screw holes 20a, 20b of the plate 12. The plate has a narrowed-width bridge portion 60, and the benders are attached to the screw holes 20a, 20b located on opposite sides and closest to the bridge portion 60 and about two threaded screw holes 22a, 22b, each provided with short drill guides 24. In order to apply a force to effect convex bending of the plate (relative to the upper surface 14 of the plate), the foot 38 of each bender is inserted into the respective hole 20a, 20b with its toe 42 oriented toward the bridge portion. With respect to each toe, as described above with respect to FIGS. 6-9, the upper surface 44 of the toe extends in contact with the wall 29 of the relief surface 28 at the end of the respective hole 20a, 20b, and the lower surface 46 extends substantially co-planar with the lower surface 16 of the plate 12. The shoulders 36 rest on the upper surface 14 of the plate and are positioned laterally outward relative to the toes 42 (in relation to the longitudinal axis $A_P$ of the plate). Given that the lever arms 30 are laterally offset to one side of the foot 38, the two lever arms 30a, 30b can cross each other over the plate at 62 without interference, with one side of each lever arm extending through a plane parallel to the other (which can be the same plane) and parallel to the longitudinal axis of said plate. The bender arms 10a, 10b are then grasped at the second ends 34a, 34b and forced in the direction of the arrows 64, 66. This causes the lever arms 30a, 30b to rotate about the fulcrums defined by the shoulders 36a, 36b seated on the upper surface 14 of the plate, and force the upper surface 44 of the toe 42 against the wall 29 of the relief 28 to effect a convex bending of the plate (relative to the upper surface of the plate) centered about the bridge portion 60. A bend of 10° to 15° is reasonably accomplished with the benders. The undercuts 48 provide clearance over the short drill guides 24 and space for rotational levering of the benders about the fulcrums (shoulders 36).

Figure 11:
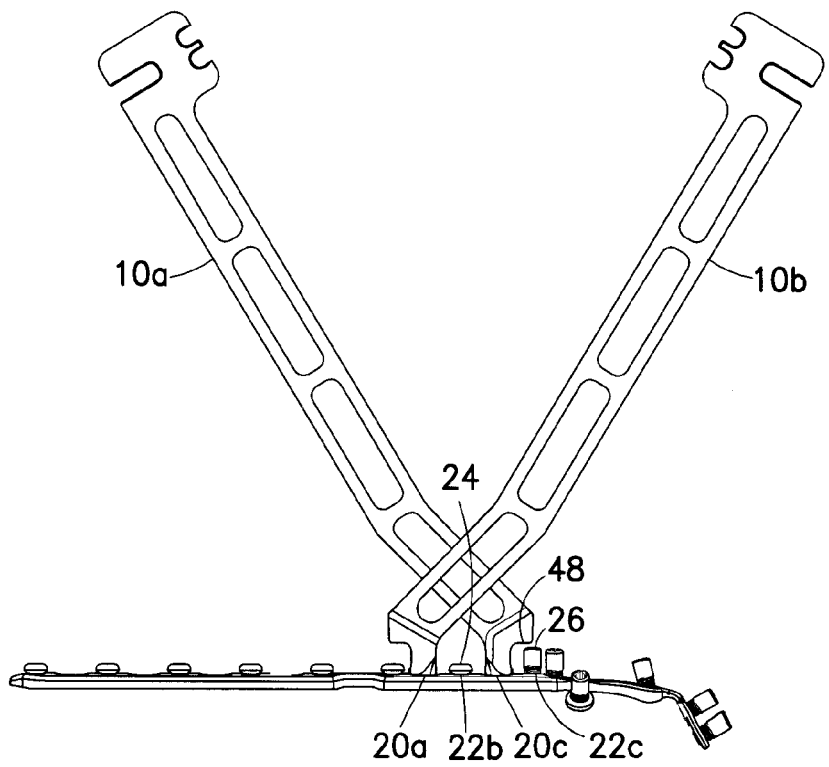
FIG. 11 illustrates an assembly of a pair of plate benders according to a first embodiment of the invention coupled to the plate in a second arrangement.

Turning to FIG. 11, the plate benders 10a, 10b may similarly be coupled to oblong screw holes 22b, 22c which immediately surround the threaded screw hole 22b provided with short drill guide 24. In such configuration it is noted that the undercut 48 at the first end 32 of plate bender 10a allows the bender to be positioned undercut 48 to the threaded screw hole 22c provided with tall drill guide 26, with the relief extending over the tall drill guide 26. Forcing the bender arms 10a, 10b in the same direction as in FIG. 10 will result in convex bending of the plate centered about the threaded screw hole 22b. A bend of 10° to 15° is reasonably accomplished with the benders.

Figure 12:
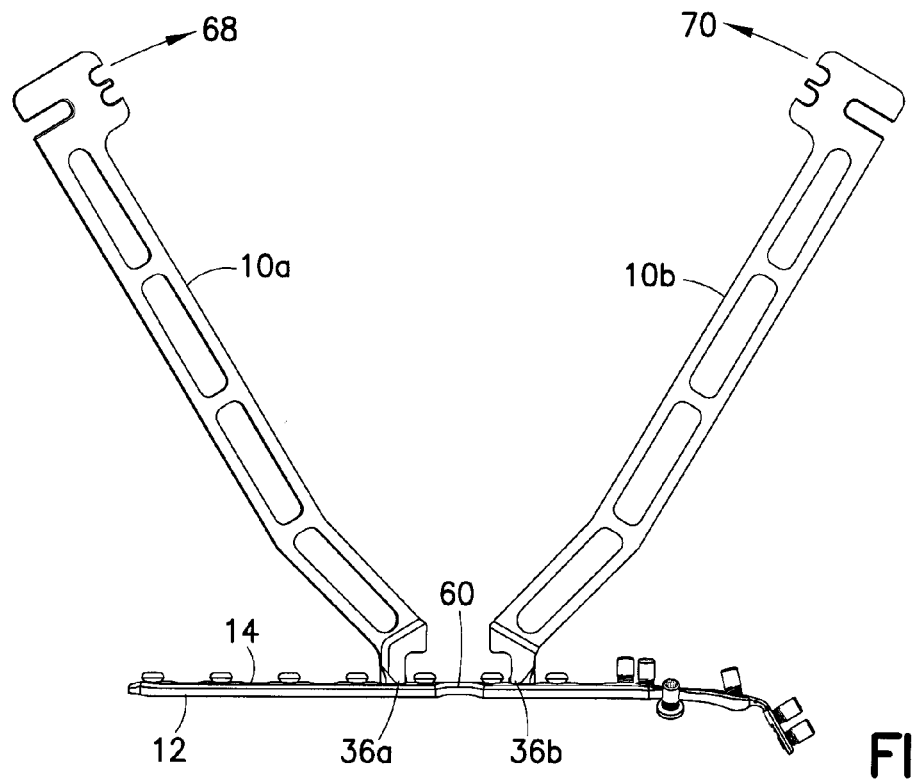
FIG. 12 illustrates an assembly of a pair of plate benders according to a first embodiment of the invention coupled to the plate in a third arrangement.

Referring now to FIG. 12, the benders 10a, 10b are shown positioned in the same non-threaded oblong screw holes 22a, 22b as in FIG. 10. However, the orientation of the benders is reversed from that shown in FIG. 10, with the toes 42 (oriented outward relative to the bridge portion 60, and the shoulders 36a, 36b provided in a medial relationship relative to the toes 42 (in relation to the longitudinal axis of the plate). When manual force is applied to the benders in the direction of the arrows 68, 70, the ends of the plate are bent upwards about the bridge in a concave manner (relative to the upper surface 14 of the plate 12). A bend of 10° to 15° is reasonably accomplished with the benders.

Figure 13:
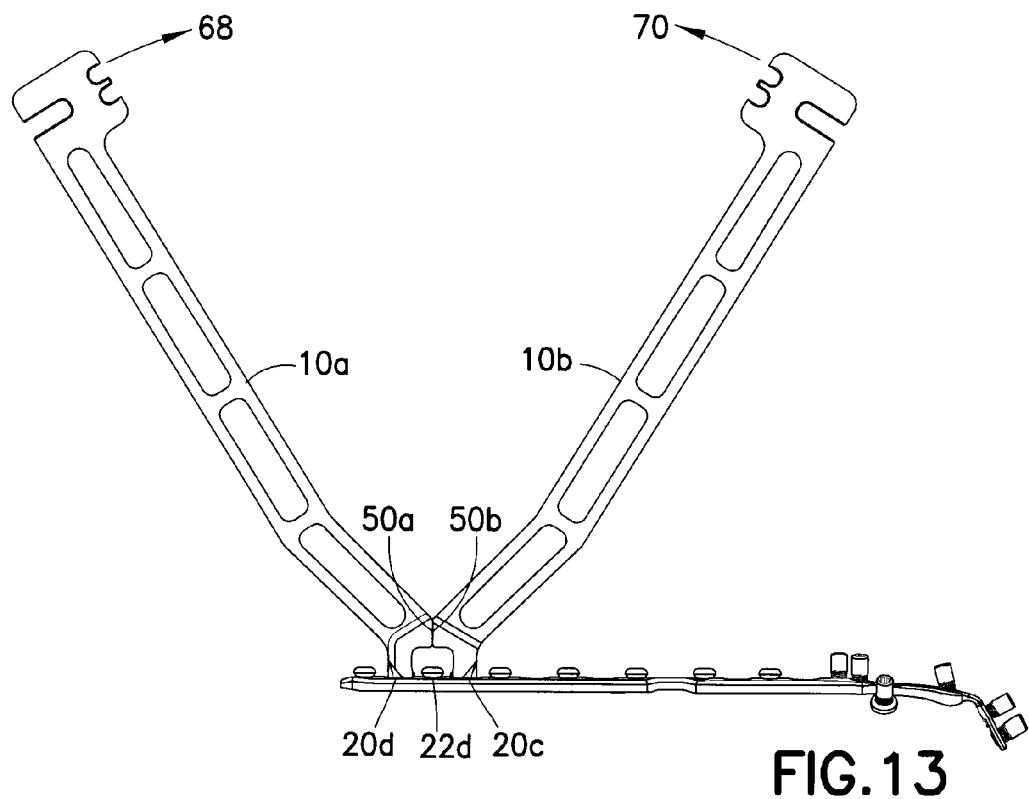
FIG. 13 illustrates an assembly of a pair of plate benders according to a first embodiment of the invention coupled to the plate in a fourth arrangement.

Turning now to FIG. 13, the benders 10a, 10b are shown positioned in a similar orientation as FIG. 12, and about a single threaded screw hole 22d. In such configuration, the stops 50a, 50b on respective benders 10a, 10b abut each other to prevent forcing the benders in the directions of the arrows 68, 70. This is because concave bending centered at a single threaded hole 22d that is located between two non-threaded oblong screw holes 20d, 20e can distort the threads of the threaded hole 22d and thereby prevent insertion of a threaded fastener therethrough. The stops 50 prohibit forcing the benders in such manner.

Figure 14:
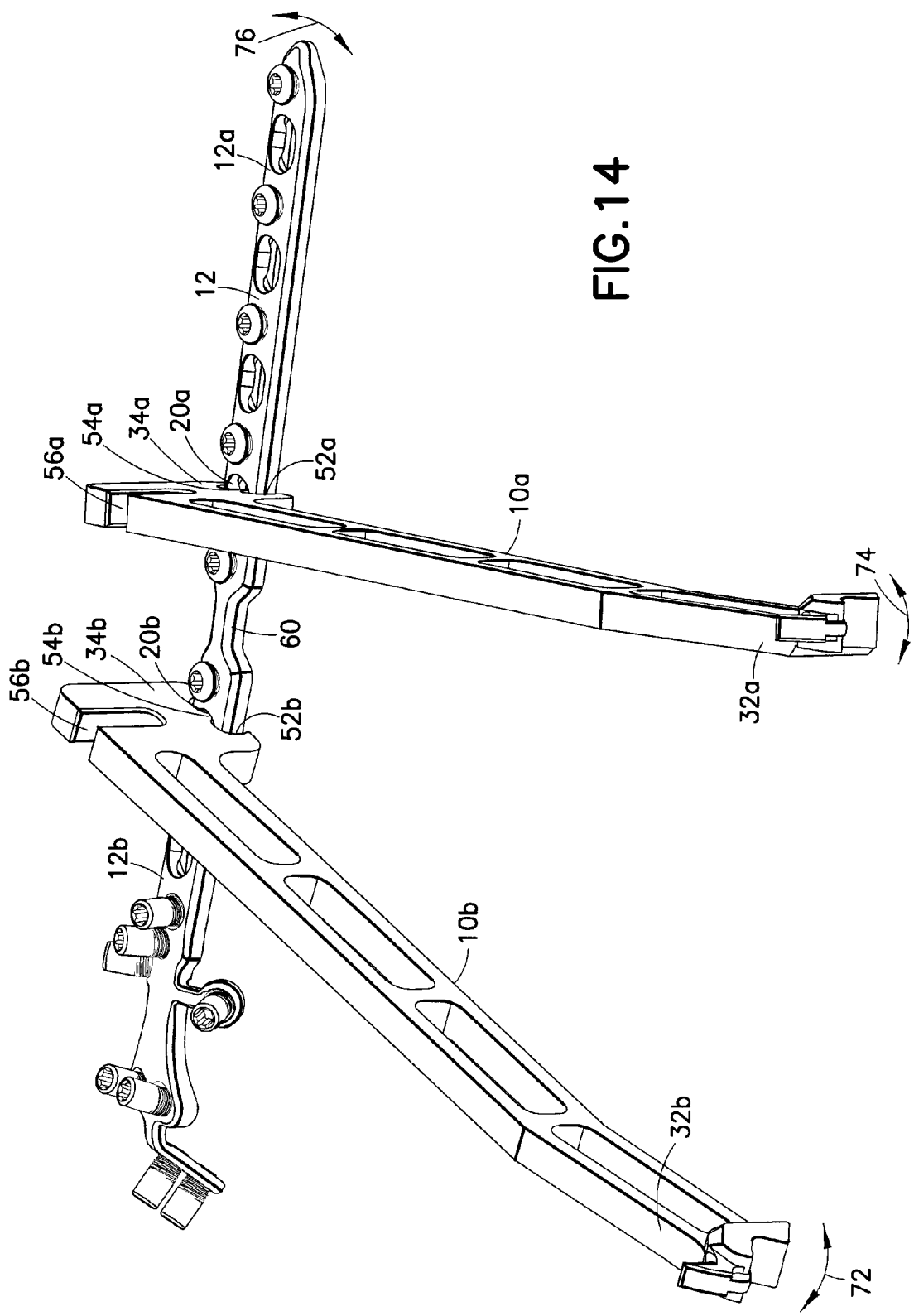
FIG. 14 is a top perspective view of an assembly of a pair of plate benders according to a first embodiment of the invention coupled to a plate at second ends of the plate benders to effect in-plane bending of the plate.
Figure 15:
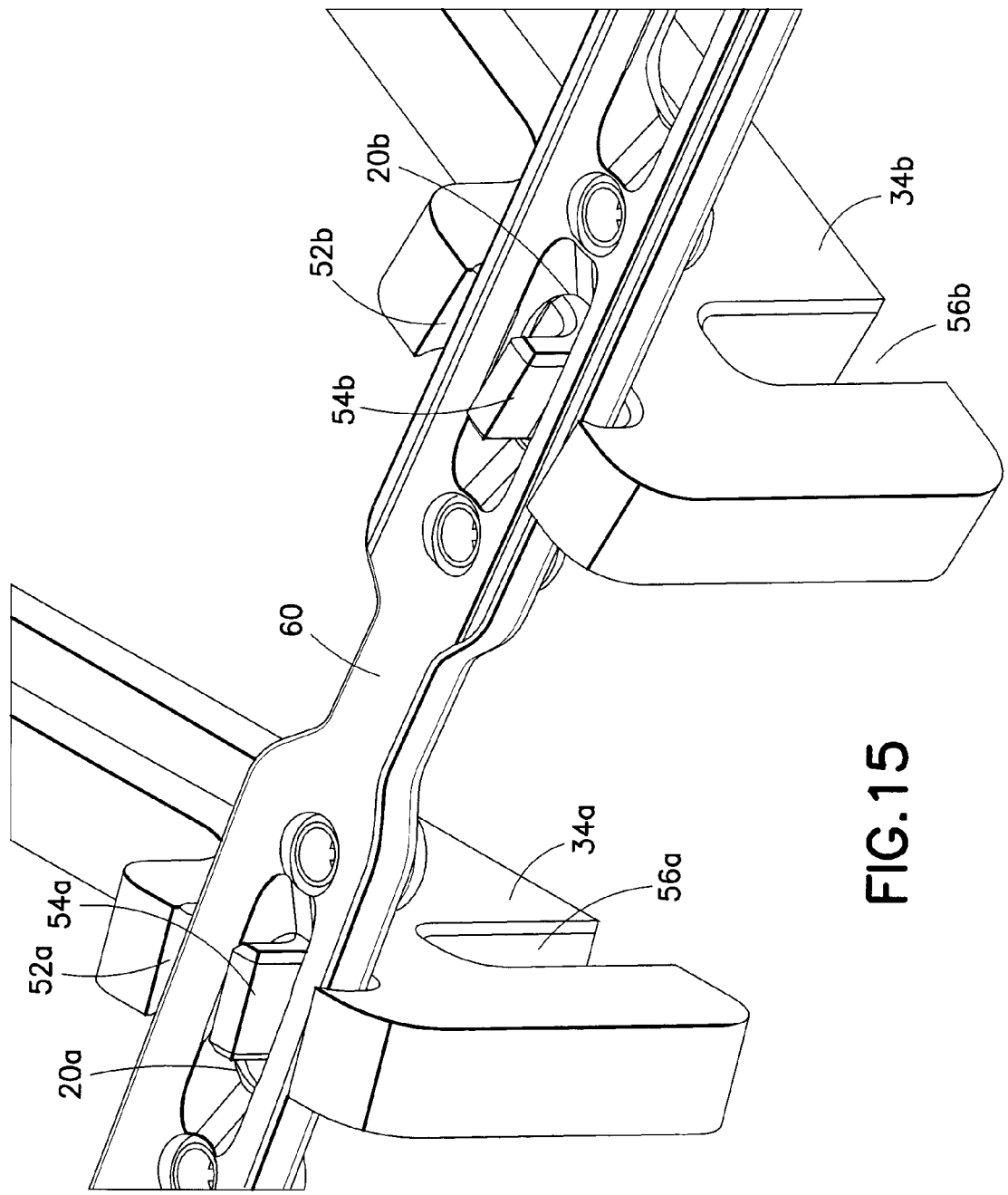
FIG. 15 is a bottom perspective view of the assembly of FIG. 14.
Figures 16, 17:
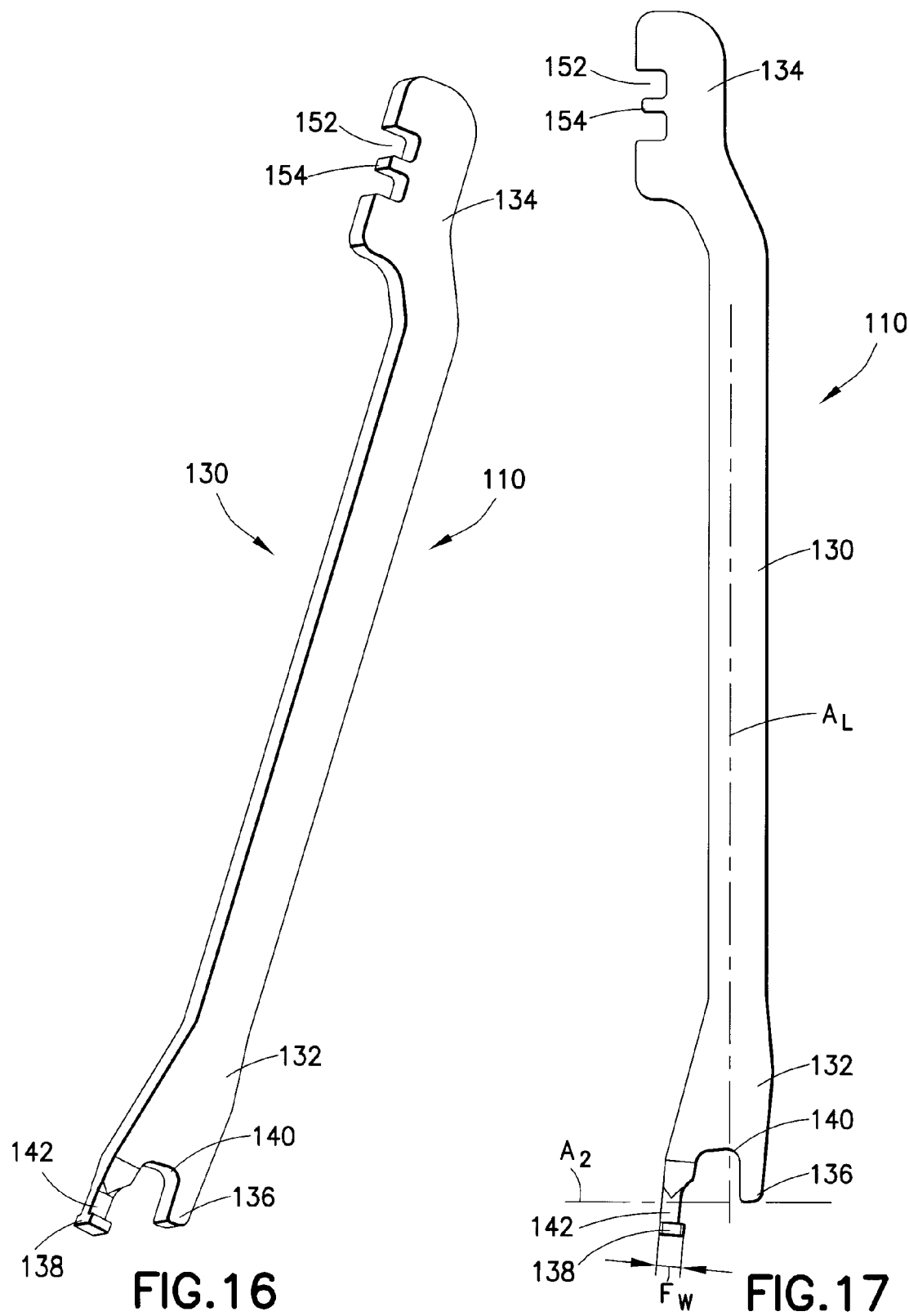
FIG. 16 is a perspective view of a plate bender according to a second embodiment of the invention.
FIG. 17 is a side elevation view of a plate bender according to a second embodiment of the invention.
Figure 18:
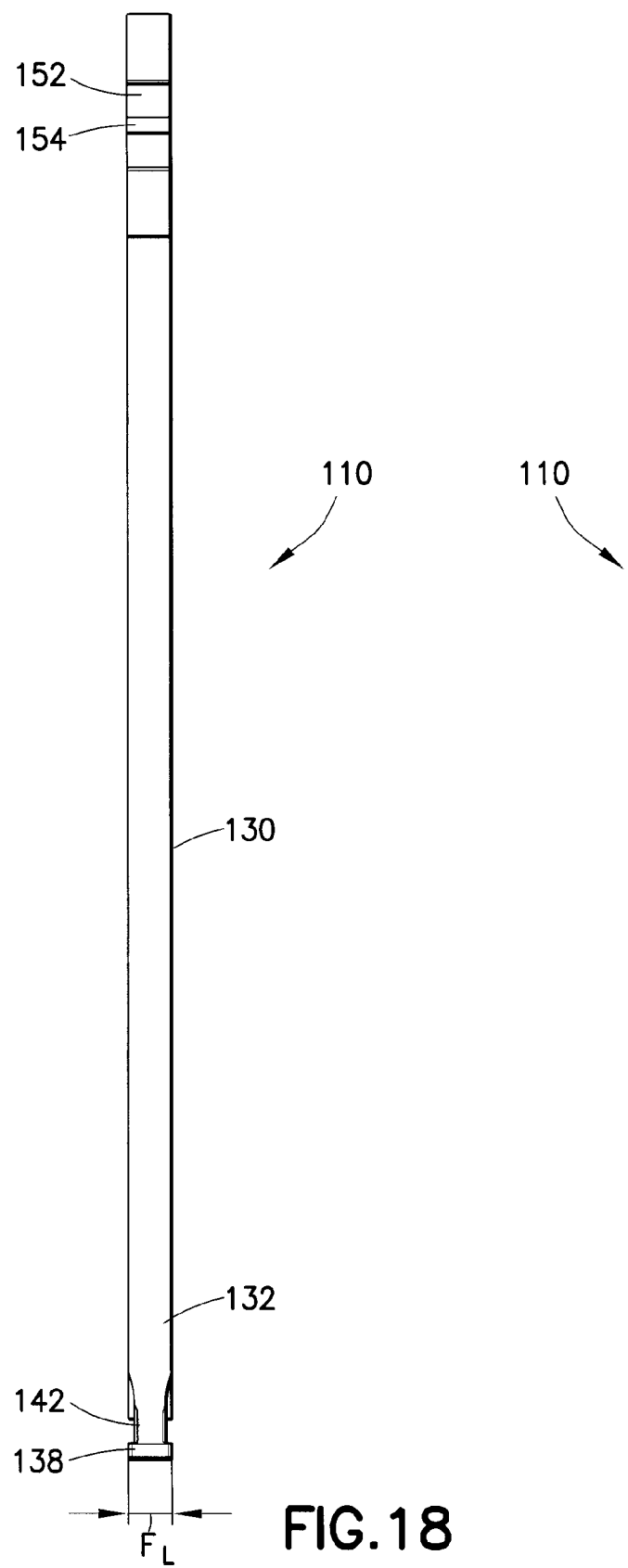
FIG. 18 is a first lateral view of a plate bender according to a second embodiment of the invention.
Figure 19:
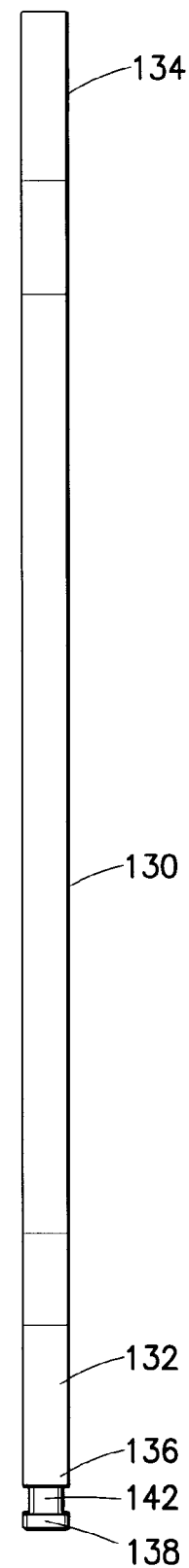
FIG. 19 is a second lateral view of a plate bender, opposite the first lateral view, according to a second embodiment of the invention.

Referring now to FIGS. 14 and 15, a pair of benders 10a, 10b are shown attached to the plate 12 in a manner to effect in-plane bending of the plate. The cut-outs 52a, 52b at the second ends 34a, 34b of the benders 10a, 10b are provided width-wise over the plate at respective elongate non-threaded plate holes 20a, 20b (on either side of narrow-width bridge 60), with the dividers 54a, 54b of the cut-outs 52a, 52b extending top-down into the holes 20a, 20b. The dividers 54a, 54b stabilize the benders on the plate 12. When manual force is applied to the second first ends 32a, 32b of the benders in the direction of either or both arrows 72, 74; that is, both benders may be moved or one bender may be moved while the other is held stationary, the plate is bent in plane about bridge 60 to cause a first portion of the plate 12a (on one side of the bridge 60) to be moved in plane relative to a second portion of the plate 12b (on the other side of the bridge 60) in the direction of arrow 76.

Still referring to FIGS. 14 and 15, the slot at the second end 34a, 34b of each bender 10a, 10b may also be guided laterally over a portion of the plate, with the thickness $T_P$ of the plate accommodated by the slot and the width $W_P$ of the plate completely received in the slot or substantially received (e.g., at least eighty percent accommodated) in the slot (see dimensions in FIG. 5). When the benders 10a, 10b are attached in this manner and a manual force is applied at the first ends of the benders to result in a torque being applied to the plate between the benders, the plate can be twisted as necessary to accommodate the bone anatomy.

Figure 20:
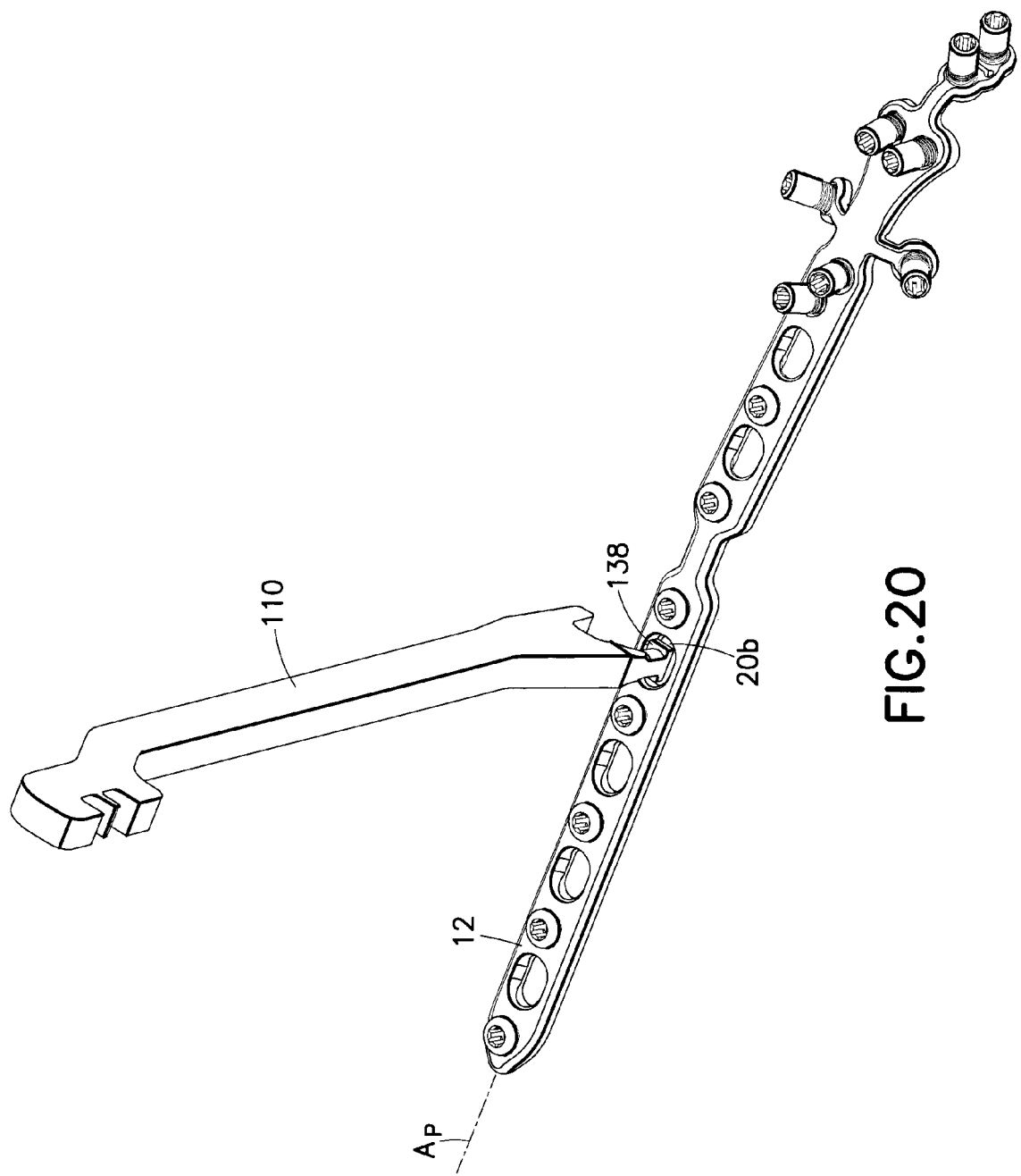
FIG. 20 is a perspective view of the first embodiment of the plate bender as it is assembled to a bone plate.
Figure 22:
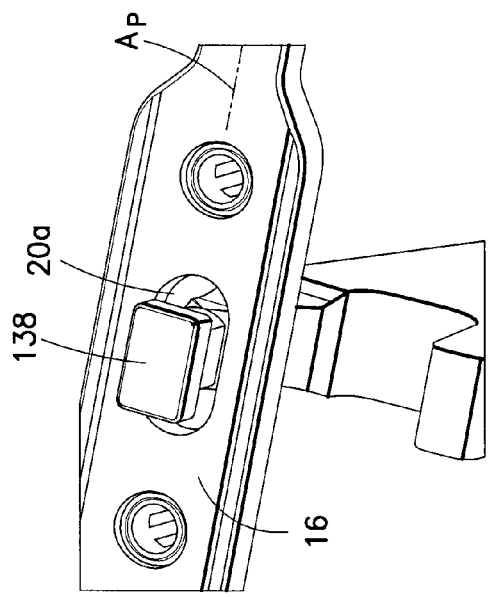
FIGS. 21 through 24 illustrate engagement of the foot at the first end of the plate bender at an oblong hole of the plate.
Figure 24:
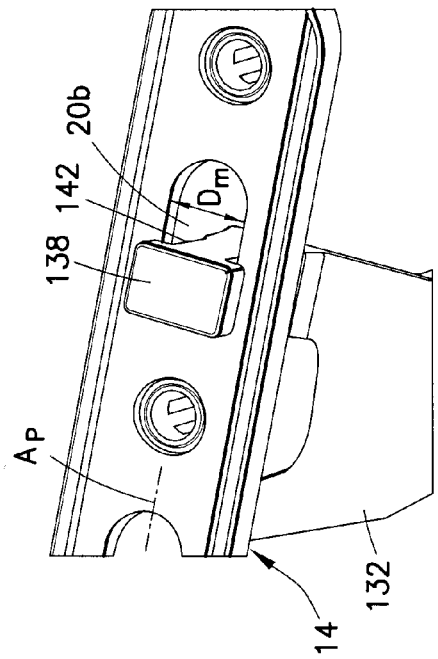
Figure 21:
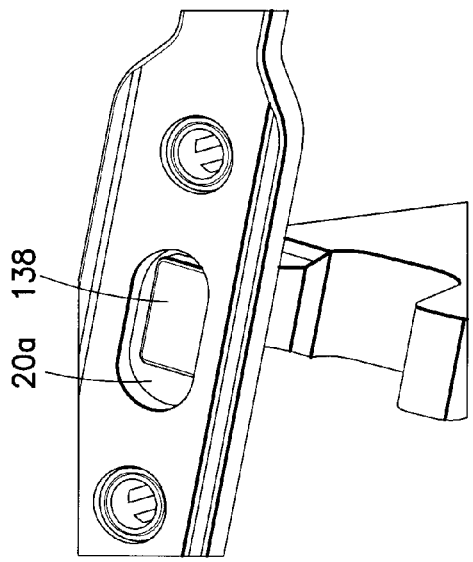
Figure 23:
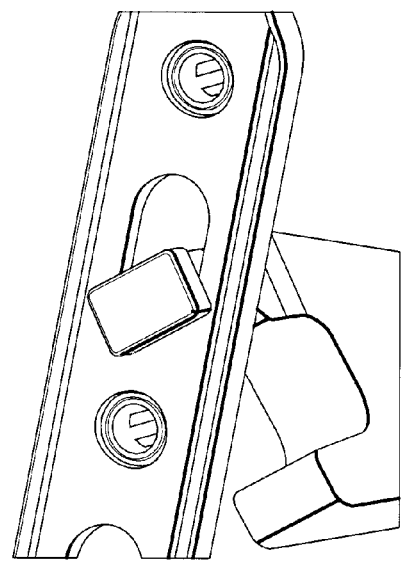

Turning now to FIGS. 16-19, a second embodiment of a plate bender 110, generally similar to plate bender 10, is shown. The plate bender 110 has a lever arm 130 with a first end 132 and an opposite second end 134. The first end 132 includes a shoulder 136 defining a fulcrum, and a foot 138 extending further along the bender than the shoulder 136. An arched recess 140 is defined between the shoulder 136 and the foot 138 such that the shoulder 136 and foot 138 are longitudinally displaced relative to an axis $A_2$ that extends transverse to the longitudinal axis $A_L$ of the lever arm 130. The foot 138 has a length $F_L$ and a width $F_W$, and the length is oriented transverse to the extension of axis $A_2$. As shown in FIGS. 20-22, in order for the foot 138 to be received through an oblong screw hole 20b the foot 138 must be rotated such that the width $F_W$ is substantially aligned with the axis $A_P$ of the plate 12. When the foot is passed through the hole 20b to clear the lower surface 16 of the plate (FIG. 22), the bender 110 is then rotated (FIG. 23) until that the shoulder 136 rests on the upper surface 14 of the plate, with the axis $A_2$ (FIG. 17) substantially aligned with the axis $A_P$ through the plate (FIG. 24). Referring to FIGS. 16-19 and 24, the first end 132 defines a reduced-width neck 142 above the foot 138 that accommodates the reduced dimension of the minor diameter $D_m$ of the oblong screw hole 20b once the bender is in the rotated and engaged position. The foot 138 and neck 142 thereby assume an inverted T-shape. Because of the design of the foot 138, the bender may be used with a plate that has a relative standard shape surrounding the perimeter of the screw hole 20b; i.e., the screw hole does not necessarily have a relief portion at the ends thereof.

Referring back to FIGS. 16-19, the second end 134 of the bender 110 has features similar to bender 10. Shown is cutout 152 with divider 154 which operates in the same manner as cutout 52 and divider 54. Optionally, a deep slot (as shown at reference numeral 56 in FIGS. 1-4 for bender 10) can also be provided which would operate in the same manner as described above with respect to such structure.

Figure 25:
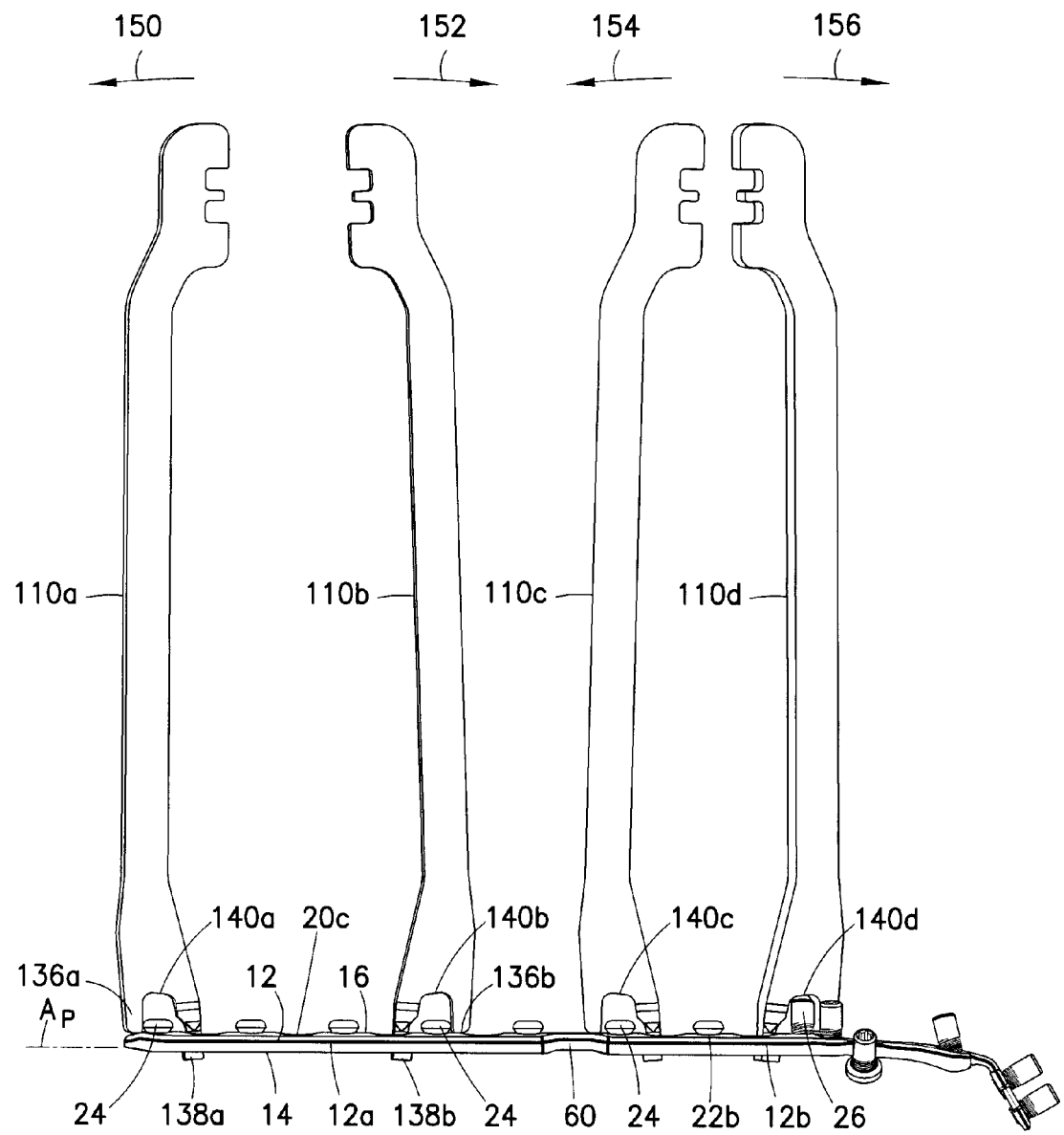
FIG. 25 is a side elevation of plate benders according to the second embodiment of the invention coupled to a bone plate.

FIG. 25 illustrates two pairs of benders coupled to plate 12. It should be appreciated that a single pair of benders are generally used on a plate at any one time. Two pairs are shown to more fully and readily illustrate how the benders function along different portions of the plate. Benders 110a and 110b are shown coupled to a first portion 12a of the plate 12. With the benders 110a, 110b attached to the plate, the shoulders 136a, 136b seat on the upper surface 14 of the plate and the feet 138a, 138b are engaged to the lower surface 16 of the plate. The benders are oriented in opposite directions, such that the shoulders are located laterally outward on the longitudinal axis $A_P$ of the plate. The recesses 140a 140b extend over the short drill guides 24, 24 seated in the plate between the shoulders and the feet. When the benders are forced in the direction of the arrows 150, 152, the first portion 12a between the benders 110a, 110b is longitudinally bent in a convex manner relative to the upper surface 14 of the plate, with the bend centered about hole 20c. A bend of 10° to 15° is reasonably accomplished with the benders.

Benders 110c, 110d are engaged to the second portion 12b of plate 12, with recess 140c extending over a short drill guide 24 and recess 140d extending over a tall drill guide 26. When benders are respectively forced in the directions of arrows 154, 156, the second plate portion between benders 110c, 110d is convexly bent relative to the upper surface 14 of the plate, with the bend centered about hole 22b. A bend of 10° to 15° is reasonably accomplished with the benders. Even after convex bending, a fixed-angle fastener with a threaded head can still be engaged within the threaded hole 22b.

Benders 110b, 110c are engaged on opposite sides of bridge 60 of the plate 12. If they are bent towards each other in the direction of arrows 154, 156, the plate is subject to a concave bend about the bridge 60. Conversely, if benders 110a, 110d, also on opposite sides of bridge 60, are bent away from each other in the direction of arrows 150, 156, the plate is subject to a convex bend about the bridge 60.

There have been described and illustrated herein embodiments of a plate bender, a plate, and methods of bending a plate. While particular embodiments of the invention have been described, it is not intended that the invention be limited thereto, as it is intended that the invention be as broad in scope as the art will allow and that the specification be read likewise. It will be appreciated by those skilled in the art that yet other modifications could be made to the provided invention without deviating from its spirit and scope as claimed.

What is claimed is:

1. A bender bar for bending a bone plate, the bone plate having an upper surface, a lower surface, a thickness defined by the distance between the upper and lower surfaces, and a plurality of oblong screw holes passing through the upper and lower surfaces, the oblong screw holes having a major diameter and a relatively transverse minor diameter, said major diameters of said oblong screw holes extending parallel to a longitudinal axis of said plate, said bender bar comprising:
   a) an elongate lever arm having a first end and a second end;
   b) a fulcrum at said first end for contacting the upper surface of the bone plate; and
   c) a foot at said first end sized to extend through said oblong screw hole and contact the lower surface of the bone plate at a periphery of the screw hole, such that said fulcrum and said foot are disposable on the upper and lower surface on opposing sides of the plate, and said foot and said fulcrum situated to be longitudinally displaced from each other along the longitudinal axis of the plate,
   wherein said second end of said lever arm includes a first side having a cut-out provided with a central divider, said cut-out having a depth generally corresponding to the thickness of the plate and a length to extend widthwise across the plate, and the divider positioned and sized to extend within the oblong screw hole of the plate.

2. A bender bar according to claim 1, wherein:
said bender bar consists of a unitary piece of metal.

3. A bender bar according to claim 1, wherein:
said lever arm includes a bend along its length to increase mechanical advantage of said lever arm, said bend located nearer said first end than said second end.

4. A bender bar according to claim 1, wherein:
said foot extends in a first direction, said foot includes upper and lower surfaces, and said upper and lower surfaces are angled relative to each other in said first direction so as to have a reduced thickness in said first direction.

5. A bender bar according to claim 1, wherein:
said fulcrum includes shoulders spaced apart on either side of the said foot in a widthwise direction.

6. A bender bar according to claim 1, wherein:
said lever arm defines a longitudinal axis, and when said longitudinal axis is oriented vertical with said second end of said lever arm located vertically above said first end of said lever arm, said foot extends lower than said fulcrum, said foot including a width and a length, said length extending transverse to a direction of displacement between said foot and said fulcrum.

7. A bender bar according to claim 6, wherein:
said first end includes a tapered neck above said foot.

8. A bender bar according to claim 6, wherein:
a recess is provided between said foot and said fulcrum.

9. A bender bar according to claim 1, wherein:
said second end includes a second side opposite said first side, said second side having a slot with a depth that accommodates at least eighty percent of the width of the plate and a width that accommodates the entire thickness of a portion of the plate.

10. A bender bar for bending a bone plate, the bone plate having an upper surface, a lower surface, a thickness defined by the distance between the upper and lower surfaces, and a plurality of oblong screw holes passing through the upper and lower surfaces, the oblong screw holes having a major diameter and a relatively transverse minor diameter, said major diameters of said oblong screw holes extending parallel to a longitudinal axis of said plate, said bender bar comprising:
   a) an elongate lever arm;
   b) a fulcrum at a first end of said lever arm for contacting the upper surface of the bone plate;
   c) a foot at said first end of said lever arm sized to extend through said oblong screw hole and contact the lower surface of the bone plate at a periphery of the screw hole, such that said fulcrum and said foot are disposable on the opposing upper and lower surfaces of the plate, and said foot and said fulcrum situated to be longitudinally displaced from each other along the longitudinal axis of the plate; and d) a second end of said lever including a first side having a cut-out provided with a central divider, said cut-out having a depth generally corresponding to the thickness of the plate and a length to extend widthwise across the plate, and the divider positioned and sized within the cut-out to extend within the oblong screw hole of the plate, wherein said bender bar consists of a unitary piece of metal.

11. A bender bar according to claim 10, wherein:
a plane bisects said fulcrum and said foot, and said plane extends parallel to but does not bisect said lever arm.

12. A bender bar according to claim 11, wherein:
said second end includes a second side opposite said first side, said second side having a slot with a depth that accommodates at least eighty percent of the width of the plate and a width that accommodates the entire thickness of a portion of the plate.

13. A plate bender system, comprising:
a) a bone plate having an upper surface, a lower surface, a thickness defined by the distance between said upper and lower surfaces, and a plurality of oblong screw holes passing through said upper and lower surfaces, said upper surface defining a major diameter and a relatively transverse minor diameter for each oblong screw hole; said major diameters extending parallel to a longitudinal axis of said plate; and
b) a pair of plate benders, each bender comprising,
  i) an elongate lever arm having a first end and a second end,
  ii) a fulcrum at the first end for contacting said upper surface of said bone plate, and
  iii) a foot extending from said first end for contacting said lower surface of said bone plate, said foot received through one of said plurality of oblong screw holes and contacting said lower surface of the plate at a periphery of said screw hole, such that said fulcrum and said foot are disposed on opposite sides of said plate and said bender is coupled to said plate, said foot and said fulcrum being laterally displaced from each other along said longitudinal axis of said plate when said bender is coupled to said plate,
wherein when a sufficient force is applied to said lever arms of each of said benders about said fulcrum when said bender is coupled to said plate, a bending force is applied by said foot to said lower surface of said plate to effect bending of said plate.

14. A plate bender system according to claim 13, wherein:
said plate defines a relief portion extending from the major diameter of each said oblong screw hole, said relief portion provided with a sloped surface that extends down at an angle to said lower surface, and said foot defines a toe that has an upper sloped surface sloped at the angle and that engages said sloped surface.

15. A plate bender system according to claim 14, wherein:
said angle is 30°±10°.

16. A plate bender system according to claim 14, wherein:
said fulcrum includes shoulders spaced apart on either side of the said foot in a widthwise direction.

17. A plate bender system according to claim 13, wherein:
said plate includes threaded screw holes, a first portion, a second portion, and narrowed-width bridge portion between said first and second portions,
wherein in each of said first and second portions said threaded and non-threaded screw holes are arranged in an alternating manner, with threaded screw holes located adjacent the bridge portion.

18. A plate bender system according to claim 13, further comprising:
tubular drill guides,
wherein said plate includes threaded screw holes alternating with said non-threaded screw holes, and said tubular drill guides are pre-assembled into said threaded screw holes.

19. A plate bender system according to claim 18, wherein:
said tubular drill guides are provided in a plurality of lengths such that said guides extend a plurality of heights above said upper surface of said plate.

20. A plate bender system according to claim 18, wherein:
said first end of each said plate bender includes an undercut that can provide clearance over a tubular drill guide when said plate bender is coupled to said plate.

21. A plate bender system according to claim 13, wherein:
said first end of each said plate bender includes a stop that longitudinally offset from said fulcrum and elevated relative to said upper surface of said plate, wherein said stop prevents movement of said benders toward each other when in contact with the stop of another bender of said pair of benders.

22. A plate bender system according to claim 13, wherein:
said fulcrum has a width, and said lever arm is laterally offset on said width of said fulcrum such that said pair of benders may be pass each other with each lever arm extending in a plane parallel to the other and parallel to the longitudinal axis of said plate.

23. A bender bar according to claim 1, wherein:
when said foot is extended through the oblong screw hole and said fulcrum is position on the upper surface of the bone plate, rotation of said lever arm about said fulcrum and through a plane extending through said lever arm, said fulcrum, and said foot causes said foot to provide a plate bending force against the lower surface of the bone plate.

24. A bender bar according to claim 1, wherein:
a plane bisects said fulcrum and said foot, and said plane extends parallel to but does not bisect said lever arm.

25. A bender bar according to claim 4, wherein said upper surface of said foot is oriented perpendicular to a longitudinal axis through said second end of said lever arm.

26. A bender bar according to claim 24, wherein said upper and lower surfaces of said foot define a wedge that tapers in a direction opposite said fulcrum.

27. A bender bar according to claim 4, wherein said upper and lower surfaces of said foot define a wedge that tapers in a direction opposite said fulcrum.

28. A plate bender system according to claim 13, wherein each said bender bar is independent of the other.

29. A kit for bending a bone plate, the bone plate having an upper surface, a lower surface, a thickness defined by the distance between the upper and lower surfaces, and a plurality of oblong screw holes passing through the upper and lower surfaces, the oblong screw holes having a major diameter and a relatively transverse minor diameter, said major diameters of said oblong screw holes extending parallel to a longitudinal axis of said plate, said kit comprising:
a pair of bender bars, each said bender bar independent of the other, each said bender bar having,
  a) an elongate lever arm having a first end and a second end;
  b) a fulcrum at said first end for contacting the upper surface of the bone plate; and c) a foot at said first end sized to extend through said oblong screw hole and contact the lower surface of the bone plate at a periphery of the screw hole, such that said fulcrum and said foot are disposable on the upper and lower surface on opposing sides of the plate, and said foot and said fulcrum situated to be longitudinally displaced from each other along the longitudinal axis of the plate, wherein said foot of each of said pair of bender bars can be inserted into a separate one of said oblong screw holes and said bender bars can be operated together to bend the bone plate along the longitudinal axis of the bone plate.

\* \* \* \* \*